United States Patent [19]

Morrison et al.

[11] Patent Number: 5,045,466
[45] Date of Patent: Sep. 3, 1991

[54] PURIFIED MAMMALIAN CELL BINDING RECEPTOR FOR BACTERIAL LIPOPOLYSACCHARIDE ENDOTOXIN AND MONOCLONAL ANTIBODY

[75] Inventors: David C. Morrison, Kearney, Mo.; Taiying Chen; Mei-Guey Lei, both of Overland Park, Kans.; Stuart W. Bright, Raytown; Linda M. Flebbe, Kansas City, both of Mo.

[73] Assignee: University of Kansas, Kansas City, Kans.

[21] Appl. No.: 376,704

[22] Filed: Jul. 7, 1989

[51] Int. Cl.$^5$ .................. C12N 5/20; C07K 15/28; C12P 21/08
[52] U.S. Cl. .................. 435/240.27; 530/387; 530/388; 435/70.21; 435/172.2; 935/104; 935/108; 935/95
[58] Field of Search .................. 530/387; 435/240.27; 935/95

[56] References Cited

PUBLICATIONS

Roeder et al., Infection and Immunity 57(4):1054–58, 1989.
Jakway et al., Fed. Proc. 44: 1297, 1985.
Wright et al., J. Exp. Med. 164: 1876–88, 1986.
Kipps & Herzenberg, pp. 108.1–108.9 in "Handbook of Expt'l Immunology", vol. 4, Herzenberg et al, Eds. 1986, Blackwell Sci. Publ.
Wright et al. J. Immunology, 144(7): 2566–71, 1990.

Primary Examiner—Esther L. Kepplinger
Assistant Examiner—Paula Hutzell
Attorney, Agent, or Firm—Felfe & Lynch

[57] ABSTRACT

The invention is directed to hydridoma cell lines and the monoclonal antibodies produced by the cell lines, where the monoclonal antibodies specifically bind to the lipopolysaccharide endotoxin binding receptor of mammalian cells. Specifically, the monoclonal antibodies binds to a cell receptor which has a molecular mass of 80 kilodaltons, and is specific for the lipid A component of the lipopolysaccharide endotoxin. The monoclonal antibodies are specific for a carbohydrate component of the binding receptor in one instance, and for a protein/peptide receptor in another.

10 Claims, 2 Drawing Sheets

FIG. 1.

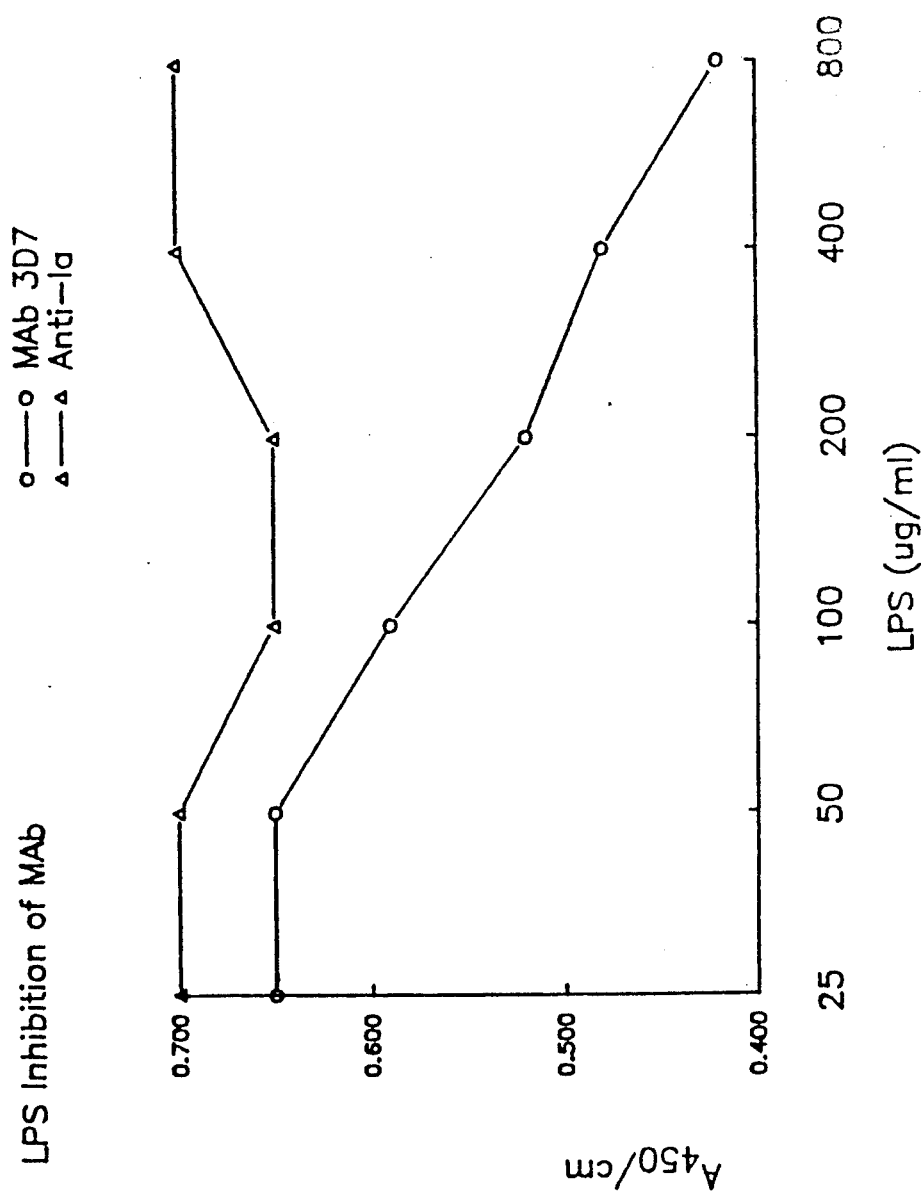

PURIFIED MAMMALIAN CELL BINDING RECEPTOR FOR BACTERIAL LIPOPOLYSACCHARIDE ENDOTOXIN AND MONOCLONAL ANTIBODY

This invention was made in part with funds from the Public Health Service under Grant No. NIH-AI-23447 from the National Institute of Allergy and Infectious Diseases. Thus the United States government retains certain rights in the invention.

SUMMARY

This invention relates to purified bacterial lipopolysaccharide (LPS) binding factor and monoclonal antibodies directed thereto.

DESCRIPTION OF THE DRAWINGS

FIG. 1 shows the capacity of mAb 3D7 to inhibit the binding of endotoxic LPS to the 80 kD LPS receptor.

FIG. 2 shows inhibition of binding of mAb 3D7 to splenocytes by LPS.

DESCRIPTION

The bacteria that can cause bacteremia, sepsis, and the septic-shock syndrome are part of the body's normal bacterial flora. If their numbers are kept in check, they are harmless. However in certain subsets of patients the bacteria have a prime environment in which to multiply. These include patients with suppressed immune systems, who receive continuous corticosteroid therapy or radiotherapy, the elderly, post-surgical patients, patients with such chronic disease as diabetes and liver disease, patients with severe burns, and infants with meningococcal infections. If, in these patients, bacteria leak into the bloodstream through the effects of surgery or catheterization or by other means, septic shock is initiated.

Researchers theorize that endotoxins, lipopolysaccharide-protein complexes found in the cell walls of gram-negative bacteria, lead to the course of the septic shock. Endotoxins are released by gram-negative bacteria and bind to receptor sites on cell walls. The toxins spur the production of numerous mediators, including tumor necrosis factor (TNF)/cachectin, interleukins 1,2 and 6, interferon, C3, procoagulant activity (tissue factor activity), as well as the PG and leukotrienes, and platelet activating factor. Symptoms which appear as the body tries to rid itself of the excess bacteria and/or endotoxin include fever, shock, disseminated intravascular coagulation, complement activation, transient leukopenia followed by leukocytosis, multisystem organ failure and death.

There are about 200,000 cases of septic shock per year in the United States, 80% of which are caused by gram-negative organisms.

Treatment for septic shock, a syndrome that can kill a patient in 48 hours, typically consists of a combination of antibiotics, vasopressors, and inotropes. A narcotic antagonist Naloxone (Narcan, Dupont) is also used. However, the results so far are only for a few patients and none have shown the agent to be efficacious (Lancet 2:699–702, 1988).

There remains a need for an effective agent that can be used to help standardize and improve treatment.

Any attempt to neutralize the endotoxin encounters the problem of the multiple endotoxins, approximately 1,000 to 10,000 which exist, even though similar in structure they may not be similar enough to react with any one antibody. The same problem may exist in obtaining mediator-directed monoclonal antibody since many mediators may contribute and multiple interdependent pathways exist for their production and/or amplification.

The use of monoclonal antibodies to counter Septic Shock toxin is also possible. Such antibodies can neutralize the endotoxin or block the endotoxin receptor site or react with the cell products which cause the shock such as TNF.

The present invention is directed to purification of the receptor glycoprotein present on the surface of mammalian peripheral blood cells (macrophages, T-cells and B-cells) which receptor is specific for bacterial LPS endotoxin. This glycoprotein is 80 KD in molecular weight.

The LPS structure is not entirely known. A common constituent component of LPS is Lipid A, Beta-(1-6)-linked diglucosamine backbone with both amide- and ester-linked long chain fatty acids as well as charged residues such as pyrophosphate, phosphorylethanolamine, and 4-amino arabinose, recognized as important for both the toxic and immunostimulatory activities of LPS. (Handbook of Endotoxin, Vol. 1. Chemistry of Endotoxin, ed. E. Th. Rietschel, Elsevier No. Holland Pub. NY, 1985). The amino acid composition is found in Table 1.

Using a radioiodinated, photoactivatable LPS probe (Wollenweber, H.W. and D.C. Morrison J. Biol. Chem. 260:15068–15074, 1985) we have identified an 80 kd LPS binding glycoprotein on murine B-lymphocytes, T-lymphocytes and macrophages (Lei, M.G. & Morrison, DC. J. Immuno. 141: 996, 1988) as well as peripheral blood mononuclear cells from many mammalian species tested which includes sheep, horse, rabbit, pig, cow, goat, dog, and man. (Roeder, D. Lei, M.G. & Morrison, DC. Infect Immuno. 57(4);1056–1058(1989) This glycoprotein is present on purified human beta-lymphocytes as well, but is missing on frog and chicken lymphoreticular cells.

We have also studied the binding of bacterial LPS endotoxin to this 80 kD protein [Mei-Guey Lei and David C. Morrison J. Immunol. 141:1006 August 1, 1988]which point to its presence in the cell membrane due to its presence in a cell membrane fraction and the binding results indicate that the 80 kD binds LPS and especially lipid A thereof.

EXAMPLE 1

The 80 kD LPS-binding protein, isoelectric point 6.5 has been purified from mouse splenocytes [T-Y Chen et al. FASEB Journal 3 No. 4 A 1082, #4969 1989]saturated with radioiodinated photoactivatable bacterial LPS endotoxin derivative cross-linked by UV irradiation. Cells were sonicated and subjected to a sucrose gradient. An LPS binding protein enriched fraction was treated with aqueous butanol at 4° C. and the biphasic mixture separated by centrifugation the receptor-LPS complex partitions in the aqueous phase. After dialysis and concentration. The aqueous extract was reduced and fractionated by SDS-PAGE.

The single radiolabelled band was electroeluted from the gel and when rerun on two-dimensional polyacrylamide gel, yielded a single radiolabelled spot.

Characterization, amino acid sequencing and molecular cloning of the cDNA for this receptor are now possible. Determination of the active binding site will allow for the design and synthesis of active receptor site analogues which will either block the ability of LPS to bind to the receptor or bind competitively to the active site without effecting cell activation.

EXAMPLE 2

The LPS binding protein from example 1 above was excized from the gel, homogenized in adjuvant and used to immunize three month old Armenian hamsters.

Armenian hamsters were immunized by subcutaneous injection of 10 ug purified LPS binding protein in complete Freund's adjuvant and boosted twice with an equal dose in incomplete Freund's adjuvant at 14 day intervals. A final boost in PBS was injected i.p. three days before the cell fusion. Splenocytes were harvested and fused to the HAT-sensitive Sp2/0 non-secretory murine myeloma cell line according to standard methods. Culture supernatants were screened by ELISA for antibodies specific for an LPS binding protein. Clones of interest were subcloned using the soft aga method and expanded to generate large volumes of culture supernatant containing the desired monoclonal antibodies.

Two monoclonal antibodies (3D7 and 5D3) were isolated following the immunization protocol (subcutaneous immunization). The monoclonals (3D7 and 5D3) are IgM and 19S molecular size. These two monoclonal antibodies are directed against two different epitopes of the 80 kD LPS-binding receptor glycoprotein. One is directed against the carbohydrate moiety and the other against the protein determinant. (Table 2). Preliminary results indicate inhibition of mouse lethality by monoclonal 5D3 antibody pretreatment (Table 3).

The use of monoclonal antibody and/or components of the antibody (e.g. Fab) to the endotoxin receptor can be employed to compete with endotoxin for binding to the receptor and thus inhibit white blood cell or endothelial cell activation. Alternatively the monoclonal can be employed as an immunogen to prepare antiidiotype antibody which may then be used to bind endotoxin and prevent its interation with target cells.

In view of the potent immunostimulatory properties of endotoxic lipopolysaccharide, the use of monoclonal antibodies can also be extended to include their incorporation into adjuvant systems to promote immunogenicity of the host to unrelated antigens.

EXAMPLE 3

Figure 1:
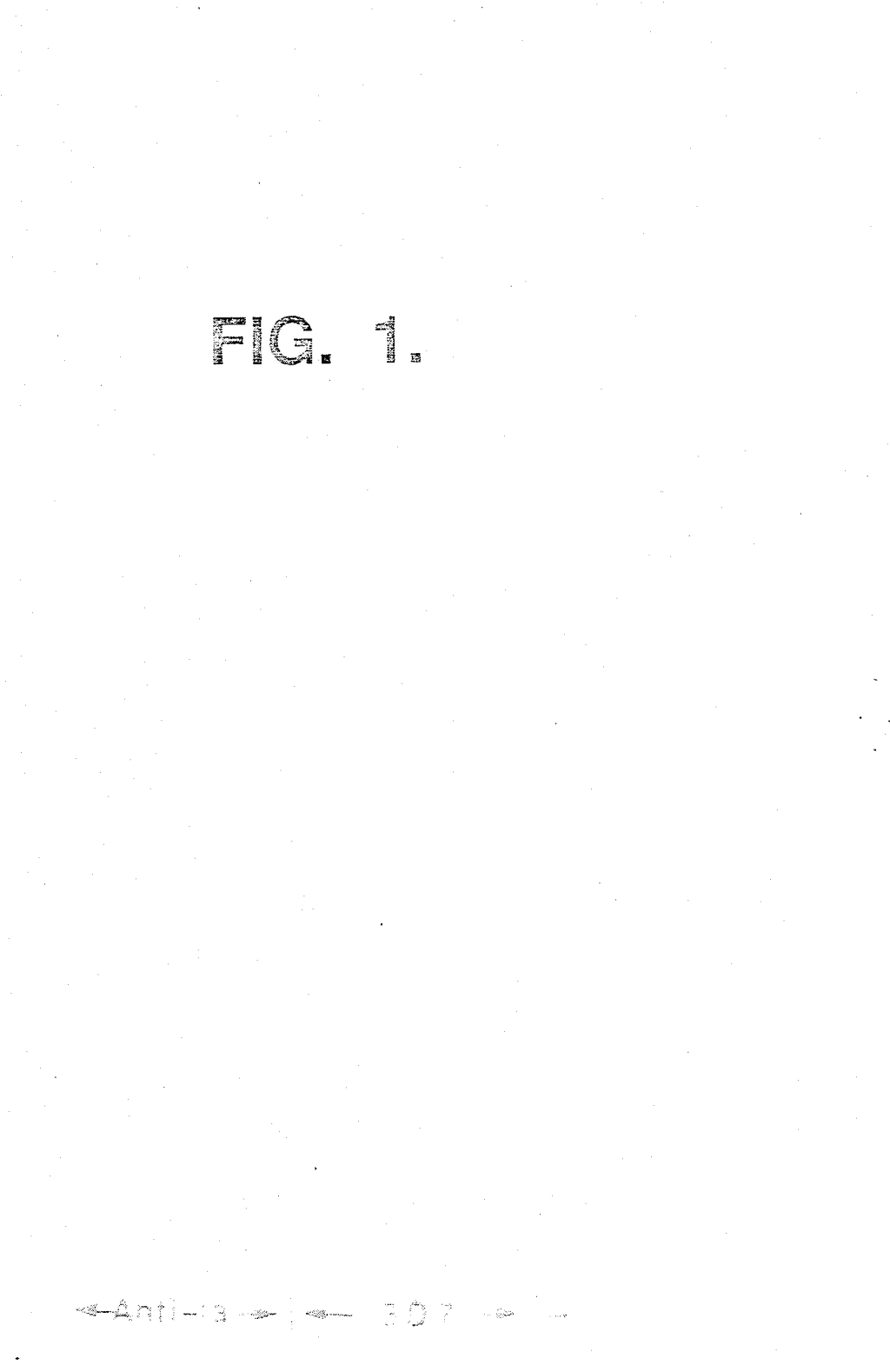

Monoclonal antibody 3D7 as obtained in Example 2 above was assessed for its capacity to inhibit the binding of endotoxic LPS to the 80 kDa LPS receptor (See FIG. 1). Increasing amounts of antibody (lanes 8-5) or an irrelevant monoclonal antibody (lanes 4-1) were added to mouse spleen cells. After 5 minutes at 37° C., $^{125}$I-ASD-LPS was added and the cells photocrosslinked by standard procedures. Solubilized cell extracts were then analyzed by SDS-PAGE and radioautographed. Control binding of LPS to the 80 kDa receptor is shown in lane 9.

EXAMPLE 4

Inhibition of binding of monoclonal mAb 3D7 to splenocytes by LPS is shown in FIG. 2. Spleen cells were bound to microtiter plates and treated with various concentrations of LPS. The cells were then washed and monoclonal antibody MAb 3D7 or an irrelevant monoclonal (anti Ia) then added. Bound antibody was assessed by ELISA.

The hybridoma cell lines secreting monoclonal antibodies 3D7 and 5D3 are on deposit at the University of Kansas Medical Center, School of Medicine, Department of Microbiology, Molecular Genetics and Immunology, 39th and Rainbow Blvd., Kansas City, Kansas 66103 and since May 4, 1989 (3D7 and 5D3) at the American Type Culture Collection (ATCC) 12301 Parklawn Drive, Rockville, MD 20852 under the designations as follows: 3D7 (10124) and 5D3 (HB10125).

TABLE 1

Amino Acid Composition of LPS-Binding Protein[1]

| Amino Acid[2] | # Residues[3] |
|---|---|
| Asp | 73 |
| Glu | 105 |
| Ser | 45 |
| Gly | 46 |
| His | 19 |
| Arg | 33 |
| Thre | 39 |
| Ala | 53 |
| Pro | 32 |
| Tyr | 27 |
| Val | 41 |
| Met | 5 |
| Ileu | 16 |
| Leu | 68 |
| Phe | 31 |
| Lys | 81 |

[1] LPS-binding protein purified from two-dimensional gels, blotted onto Immobilon and subject to acid hydrolysis and amino acid analysis
[2] Average of three independent determinations
[3] Based upon 80,000 kDa molecular mass

TABLE 2

Effect of Chemical Modification on Monoclonal Antibody Binding to Purified 80 kDa LPS Receptor

| | Absorbance at 450 nm with MoAb: | |
|---|---|---|
| Treatment[1] | 3 D 7 | 5 D 3 |
| None | 0.31 | 0.16 |
| Periodate | | |
| 1 mM | <0.01 | 0.23 |
| 10 mM | <0.01 | 0.67 |
| Protease K | | |
| 0.1 ug/ml | 0.29 | <0.01 |
| 1.0 ug/ml | 0.28 | <0.01 |

[1] Microtiter plates coated with 80 kDa LPS Receptor treated with periodate or protease K for 1.0 hour at 37° C.

TABLE 3

Protection of Mice Against Endotoxin Lethality with Purified 5D3 Monoclonal

| Pretreatment[1] | Challenge | Survivors @ 18 hours |
|---|---|---|
| saline | 0.01 μg LPS | 1/10 (10%) |
| 5D3 (75 μg) | 0.01 μg LPS | 10/10 (100%) |

[1] Mice (CF1 females, 18-22 gm) were administered either pyrogen free saline or purified 5D3 monoclonal antibody intraperitoneally in a final volume of 60 μl. One hour later mice received a second intraperitoneal injection of S. enteritidis LPS and 18 mg of D-galactosamine. Survivors were monitored hourly for the first 9 hours and then at 12 hour intervals. All control mice died within 9-12 hours. No mice given 5D3 died even after 48 hours.

What is claimed:

1. A monoclonal antibody which specifically binds to a receptor for bacterial lipopolysaccharide endotoxin which is present on mammalian peripheral blood mononuclear cells and murine B-lymphocytes, T-lymphocytes and macrophages, has a molecular weight of 80 kilodaltons as determined by SDS Page, and binds to a lipid A component of said bacterial lipopolysaccharide endotoxin.

2. A monoclonal antibody of claim 1, wherein said monoclonal antibody is produced by a hybridoma cell line or having ATCC accession number ATCC HB 10124 or ATCC HB 10125.

3. A monoclonal antibody of claim 1, wherein said monoclonal antibody is produced by a hybridoma cell line having ATCC accession number ATCC HB 10124.

4. A monoclonal antibody of claim 1, wherein said monoclonal antibody specifically binds to a protein moiety of said receptor for bacterial lipopolysaccharide endotoxin.

5. A monoclonal antibody of claim 4, wherein said monoclonal antibody is produced by a hybridoma cell line having ATCC accession number ATCC HB 10125.

6. A hybridoma cell line which produces a monoclonal antibody which specifically binds to a receptor for bacterial lipopolysaccharide endotoxin which is present on mammalian peripheral blood mononuclear cells and murine B-lymphocytes, T-lymphocytes and macrophages, has a molecular weight of 80 kilodaltons as determined by SDS-Page, and binds to a lipid A component of said bacterial lipopolysaccharide endotoxin.

7. A hybridoma cell line of claim 7 having ATCC accession number ATCC HB 10124 or ATCC HB 10125.

8. A hybridoma cell line of claim 6 having ATCC accession number ATCC HB 10124.

9. A hybridoma cell line of claim 6, wherein said monoclonal antibody specifically binds to a protein moiety of said receptor for bacterial lipopolysaccharide endotoxin.

10. A hybridoma cell line of claim 9 having ATCC accession number ATCC HB 10125.

* * * * *

UNITED STATES PATENT AND TRADEMARK OFFICE
CERTIFICATE OF CORRECTION

PATENT NO. : 5,045,466

DATED : September 3, 1991

INVENTOR(S) : David C. Morrison et al.

It is certified that error appears in the above-identified patent and that said Letters Patent is hereby corrected as shown below:

Claim 7, line 1: change "claim 7" to -- claim 6 --.

Signed and Sealed this

Twenty-seventh Day of April, 1993

Attest:

MICHAEL K. KIRK

*Attesting Officer*      Acting Commissioner of Patents and Trademarks